United States Patent [19]
Logan et al.

[11] Patent Number: 5,958,411
[45] Date of Patent: Sep. 28, 1999

[54] METHODS OF INHIBITING ECM ACCUMULATION IN THE CNS BY INHIBITION OF TGF-β

[75] Inventors: Ann Logan, Worcestershire, United Kingdom; Andrew Baird, San Diego, Calif.

[73] Assignee: The Whittier Institute for Diabetes and Endocrinology, La Jolla, Calif.

[21] Appl. No.: 08/410,573

[22] Filed: Mar. 24, 1995

Related U.S. Application Data

[63] Continuation of application No. 07/860,704, Apr. 1, 1992, abandoned.

[51] Int. Cl.⁶ .................... A61K 38/16; A61K 39/395
[52] U.S. Cl. .................... 424/158.1; 514/2; 514/12; 530/389.1; 530/387.1
[58] Field of Search .................... 514/2; 530/387.1, 530/389.1; 424/158.1

[56] References Cited

U.S. PATENT DOCUMENTS 5,583,103  12/1996  Ruoslahti et al. .................... 514/8

FOREIGN PATENT DOCUMENTS

| WO 91/02067 | 2/1991 | WIPO . |
| WO 91/04748 | 4/1991 | WIPO . |
| WO 91/10727 | 7/1991 | WIPO . |

OTHER PUBLICATIONS

Kengaku et al. (1991) Dev. Brain Res. 61, 281–284.
Shah et al. 1992 Faucet 339: 213–214.
Sammuels et al 1989 Am. J. Pathol. 134 (4): 895.
Yamaguchi et al. 1990 Nature 346:281.
Border et al 1990 Cell Diff. Devel. 32: 425–432.
Logan et al., "CF 313—In Vivo Effects of Growth Factor Agonists and Antagonists on Mammalian CNS Injury Responses" *Journal of Cellular Biochemistry* Abstracts, 20th Annual Meeting, Supplement 15F, Apr. 1, 1991–Apr. 7, 1991.
Nichols et al., "Increases in Transforming Growth Factor–β mRNA in Hippocampus During Response to Entorhinal Cortex Lesions in Intact and Adrenalectomized Rats," *J. of Neurosci. Res.* 28:134–139 (1991).
Klempt et al., "Transforming Growth Factor Beta Expression in the Rat Brain is Markedly Increased After a Hypoxic–Ischemic Insult," *Proc. 73rd Ann. Meeting Am. Endocrin. Soc.* p. 1809 (Abstract 1991).
Logan et al., "Enhanced expression of transforming growth factor β1 in the rat brain after a localized cerebral injury" *Brain Res.* 587:216–225 (1992).
Border et al. "Antagonists of transforming growth fctor–β: A novel approach to treatment of glomerulonephritis and prevention of glomerulosclerosis," *Kidney International*, 41:566–570 (1992).

Shah et al. "Reduction of tissue formation in adult rodent wound healing by manipulation of the growth factor profile," *J. Cell Biochem*, 15 (Suppl. F):198 (Apr. 1991).
Schnell and Schwab, Axonal regeneration in the rat spinal cord produced by an antibody against myelin–associated neurite growth inhibitors. *Nature* 343:269–272 (1990).
Flanders et al., Transforming Growth Factor–β1: Histochemical Localization with Antibodies to Different Epitopes. *J. Cell Biol.* 108:653–660 (1989).
Shah, M., Foreman, D.M. and Ferguson, M.W.J. Control of scarring in adult wounds by neutralising antibody to transforming growth factor β. *The Lancet* 339:213–214 (1992).
Miller, et al., Complementary DNA Cloning of the Murine Transforming Growth Factor–β3 (TGFβ3) Precursor and the Comparative Expression of TGFβ3 and TGFβ1 Messenger RNA in Murine Embryos and Adult Tissues. *Molec. Endocrinol.* 3:1926–1934 (1989).
Wilcox and Derynck, Developmental Expression of Transforming Growth Factors Alpha and Beta in Mouse Fetus. *Mol. Cell. Biol.* 8:3415–3422 (1988).
Edwards et al., Transforming growth factor beta modulates the expression of collagenase and metalloproteinase inhibitor. *EMBO* 6:1899–1904 (1987).
Laiho et al., Transforming Growth Factor–β Induction of Type–1 Plasminogen Activator Inhibitor. *J. Biol. Chem.* 262:17467–17474 (1987).
Ignotz and Massague, Cell Adhesion Protein Receptors as Targets for Transforming Growth Factor–β Action. *Cell* 51:189–197 (1987).
Krusius and Ruoslahti, Primary structure of an extracellular matrix proteoglycan core protein deduced from cloned cDNA. *PNAS (USA)* 83:7683–7687 (1986).

*Primary Examiner*—John Ulm
*Assistant Examiner*—Christine Saoud
*Attorney, Agent, or Firm*—Marshall, O'Toole, Gerstein, Murray & Borun

[57] ABSTRACT

The present invention relates to methods for preventing, suppressing or treating a CNS pathology characterized by a deleterious accumulation of extracellular matrix in a tissue by contacting the tissue with an agent that inhibits the extracellular matrix producing activity of TGF-β. The methods can be used to prevent, suppress or treat scar formation in the CNS. Agents that are useful in the present methods include neutralizing anti-TGF-β antibodies, Arg-Gly-Asp-containing peptides, decorin and its functional equivalents such as biglycan, and TGF-β antagonists. The present invention further provides methods for preventing, suppressing or treating a CNS pathology characterized by the insufficient accumulation of extracellular matrix. Agents that enhance the production of extracellular matrix, such as TGF-β, can be used in such methods. Finally, the present invention provides pharmaceutical compositions containing these agents, which can be administered to patients to inhibit or enhance the production of extracellular matrix in the CNS.

8 Claims, No Drawings

METHODS OF INHIBITING ECM ACCUMULATION IN THE CNS BY INHIBITION OF TGF-β

This application is a continuation of application Ser. No. 07/860,704, filed Apr. 1, 1992 now abandoned.

The present invention was supported in part by Grant No. DK 18811 and NS-28121 from National Institute of Health. The Government may have certain rights in this invention.

BACKGROUND OF THE INVENTION

This invention relates generally to growth factors and more specifically, to the influence of transforming growth factor-β (TGF-β) on scar formation and extracellular matrix production in the central nervous system (CNS).

Complete lesions of neural pathways in the adult mammalian CNS are rarely followed by significant functional recovery. After a penetrating injury of the brain or spinal cord, a complex sequence of tissue-specific cellular events is initiated, including a general inflammatory response, angiogenesis, widespread reactive gliosis and the formation of a dense permanent scar of mesodermal origin. These responses are accompanied by transient neuronal sprouting and synaptogenesis, but in most cases the growth responses of neurons are aborted as the glial/meningeal scar becomes organized as discussed in Maxwell et al., *Phil. Trans. R. Soc. Lond.* 328:479–499 (1990).

There are many theories to explain the failure of axonal growth after injury to the CNS. They attribute the failure to an absence of trophic cues such as growth factors (Logan, *Brit. J. Hosp. Med.* 43:428–437 (1990)) or to the release of growth inhibitory substances (Schnell & Schwab, *Nature* 343:269–272 (1990)). The mature scar, with its dense fibrous connective tissue bordered by an astrocytic glia limitans, is a physical barrier to axonal growth. It may be that deficiencies in the extracellular environment of the growing neurites restrict their growth so that they reach the scar tissue after the barrier is formed. Axonal penetration through scar tissue does not occur in the CNS.

Various pathologies are characterized by a deleterious accumulation of extracellular matrix materials. For example, in progressive glomerular disease, extracellular matrix accumulates in the mesangium or along the glomerular basement membrane, eventually causing end-stage disease and uremia. Similarly, adult or acute respiratory distress syndrome (ARDS) involves the accumulation of matrix materials in the lung, while cirrhosis of the liver is characterized by deleterious matrix accumulation evidenced by scarring in the liver.

At present, there are no therapies available to promote successful regeneration and functional reconnection of damaged neural pathways. Any clinical paradigm designed to promote regeneration of central neural pathways must include a regime for reduction of extracellular matrix deposition at the wound site.

Thus, a need exists to determine the factors that regulate accumulation of matrix components in the CNS after injury. A need also exists to control such factors to prevent, limit or treat pathogenic conditions characterized by inappropriate extracellular matrix formation in the CNS. The present invention satisfies these needs and provides related advantages as well.

SUMMARY OF THE INVENTION

The present invention relates to methods for preventing, suppressing or treating a CNS pathology characterized by a deleterious accumulation of extracellular matrix in a tissue by contacting the tissue with an agent that inhibits the extracellular matrix producing activity of TGF-β. The methods can be used to prevent, suppress or treat scar formation in the CNS.

Agents that are useful in the present methods include, for example, neutralizing anti-TGF-β antibodies, Arg-Gly-Asp-containing peptides, decorin and its functional equivalents such as biglycan. Additionally, such agents can also be TGF-β antagonists that compete with TGF-β in binding to a TGF-β receptor. Pharmaceutical compositions containing these agents can be administered to the patients to inhibit the activity of TGF-β1 in the CNS.

The present invention further relates to methods for preventing, suppressing or treating a CNS pathology characterized by an insufficient accumulation of extracellular matrix by contacting a tissue with an agent that promotes extracellular matrix formation.

DETAILED DESCRIPTION OF THE INVENTION

The present invention generally relates to CNS injuries, and more particularly the presence of TGF-β1 in injured CNS tissues. Although mRNA for TGF-β1, TGF-β2 and TGF-β3 are detectable in embryonic mouse brain, only TGF-β2 and TGF-β3 have been localized in unlesioned adult rat brain. In the experiments described below, very low levels of TGF-β1 expression were detected in the unlesioned adult rat brain both by in situ hybridization and immunostaining. This observation is in agreement with the results described in Miller et al., *Molec. Endocrinol.* 3:1926–1934 (1989) and Wilcox & Derynck, *Mol. Cell. Biol.* 8:3415–3422 (1988), in which TGF-β1 expression was not detected in adult mouse brain.

A number of growth factors are known to mediate various injury responses in peripheral tissues. In particular, TGF-β is a potent stimulator of extracellular matrix deposition in peripheral tissue wounds. TGF-β has a profound influence on extracellular matrix production, including increasing collagen, fibronectin, and proteoglycan expression. This growth factor also increases integrin expression, decreases the synthesis of proteases which degrade extracellular matrix components such as collagenase and transin, and increases the expression of protease inhibitors, such as the plasminogen activator inhibitor type 1 and the tissue specific inhibitor of metalloprotease.

TGF-β is a multifunctional cytokine that plays an important role in regulating repair and regeneration following tissue injury. Three isoforms of TGF-β, TGF-β1, 2, and 3, are expressed in mammals and to date show similar properties in vitro. Platelets contain high concentrations of TGF-β, and upon degranulation at a site of injury, release TGF-β into the surrounding tissue. TGF-β then initiates a sequence of events that promotes healing including (1) chemoattraction of monocytes, neutrophils, and fibroblasts, (2) autoinduction of TGF-β production and stimulation of monocytes to secrete interleukin-1 (IL-1), tumor necrosis factor and other cytokines, (3) induction of angiogenesis and cell proliferation, (4) control of inflammation and cell toxicity by acting as a potent immunosuppressant and inhibitor of peroxide release, and (5) increased deposition of extracellular matrix.

The effect of TGF-β on extracellular matrix is a key feature of its functional activities. TGF-β stimulates the synthesis of individual matrix components such as fibronectin, collagens and proteoglycans and simultaneously blocks matrix degradation by decreasing the synthesis of proteases and increasing the levels of protease inhibitors as described in Edwards et al., *EMBO* 6:1899 (1987) and Laiho et al., *J. Biol. Chem.* 262:17467 (1987). TGF-β also increases the expression of integrins and changes their relative proportions on the surface of cells in a manner that could facilitate adhesion to matrix as reported in Ignotz & Massague, *Cell* 51:189 (1987).

The mature form of TGF-β is comprised of two identical chains, each of 112 amino acids. The amino acid sequence of TGF-β is as follows:

Ala Leu Asp Thr Asn Tyr Cys Phe Ser Ser Thr Glu Lys
Asn Cys Cys Val Arg Gln Leu Tyr Ile Asp Phe Arg Lys
Asp Leu Gly Trp Lys Trp Ile His Glu Pro Lys Gly Tyr
His Ala Asn Phe Cys Leu Gly Pro Cys Pro Tyr Ile Trp
Ser Leu Asp Thr Gln Tyr Ser Lys Val Leu Ala Leu Tyr
Asn Gln His Asn Pro Gly Ala Ser Ala Ala Pro Cys Cys
Val Pro Gln Ala Leu Glu Pro Leu Pro Ile Val Tyr Tyr
Val Gly Arg Lys Pro Lys Val Glu Gln Leu Ser Asn Met
Ile Val Arg Ser Cys Lys Cys Ser. (SEQ. ID. NO. 1)

In peripheral tissues TGF-β is a potent stimulant for scar tissue formation characterized by the excessive accumulation of extracellular matrix components. Various agents have been found that block the stimulatory effect of TGF-β on proteoglycan production resulting in reduced extracellular matrix formation in peripheral tissues as described, for example, in Ruoslahti and Yamaguchi, *Cell* 64:867–869 (1991). Such agents include, for example, anti-TGF-β antibodies, RGD-containing peptides and decorin.

However, the role of TGF-β1 in CNS wounds was not known until the discovery relating to the present invention. The focal elevation of TGF-β1 mRNA and protein observed three days after lesion, suggests that this growth factor plays a role in regulating the CNS responses to injury. The association of TGF-β1 mRNA and protein with injury-responsive cells such as glia, neurons and vascular endothelial cells, indicates that the factor is endogenously produced, and not simply supplied to the wound via blood platelets. The observations made in this model agree with those obtained by others who have also demonstrated increased TGF-β1 mRNA in rat hippocampus after entorhinal cortex lesion by northern blot hybridization (Nicols et al., *Neurosci. Res.* 28:134–139 (1991)) and by in situ hybridization in rat cerebral cortex, striatum and hippocampus after a hypoxic-ischemic insult (Klempt et al., *Proc. 73rd Ann. Meeting Am. Endocrin. Soc.* p. 1809 (Abstract 1991)). The results are particularly surprising because the presence of TGF-β1 in injured CNS tissue was believed to be a result of a compromised blood brain barrier. However, in the studies described below, it has been shown that the blood brain barrier is regenerated before scarring occurs.

The in vivo infusion studies detailed in the examples below further evidence that TGF-β1 is a prime regulator of matrix production in the CNS after injury. A dramatic increase in fibrous matrix material deposited within the wound is observed in all animals infused with recombinant TGF-β1. Thus, in the injured CNS, as in peripheral tissues, TGF-β1 enhances matrix deposition and therefore promotes fibrous scar formation. The reactive gliosis that occurs in the neuropile surrounding the wound is apparently unaffected by the treatment as is astrocyte association into a glial membrane, suggesting that, for this part of the response at least, TGF-β1 is not a limiting trophic factor. The observed dramatic increase in number of cells of the macrophage/microglial lineage in the injured neuropile of TGF-β1 infused animals suggests an additional role in injury for TGF-β1, as a chemoattractant for blood-derived cells that themselves produce multiple trophic factors.

That TGF-β1 is produced by cells in the damaged tissue suggests that it is acting as an endogenous stimulant of scarring responses in the CNS and, in particular, of matrix deposition. Immunoneutralization of endogenous TGF-β1 activity results, in some cases, in a dramatic reduction in matrix deposition in the CNS wound, thus establishing an intrinsic activity for endogenous TGF-β1. The results suggest that a reduction of the dense permanent scar that is deposited at the site of injury, and which blocks the path of regenerating neurons, is one step towards achieving functional reconnection of damaged neural pathways to their target organs.

The reduction in macrophage/microglial cell number in the immunoneutralized wound and the lack of an organized glial limiting membrane, despite the presence of a clear reactive gliosis response, again suggests that TGF-β1 is exerting multiple effects in these damaged tissues. Thus, endogenous TGF-β1 may act as a chemoattractant for blood-derived cells and for activated astrocytes, as well as a potent desmoplastic agent, promoting matrix deposition by the invading fibroblasts. The functional consequences of the immunoneutralizing effects reported here are at present unknown, but in this study we could see no evidence of active nerve regeneration (assessed using GAP 43 and RT 97 antibodies as markers of regenerating axons) in any of the treated animals after fourteen days. Presumably, additional neurotrophic agents may be required to sustain this aspect of the injury response.

In this study, although the response to infused recombinant TGF-β1 was consistent in all animals, the response to TGF-β1 immunoneutralization was consistently more variable. This variability may be attributed to the effective concentration and bioactivity of the infused antibody within the target tissue and to potential compensatory mechanisms of other trophic factors which may be contributing to the regulation of the cellular responses examined.

The infusion experiments described below are the first to directly address the question of whether scar production in the CNS is amenable to modulation in vivo. While the modification of the injury response has been achieved using TGF-β1-related molecules, immunoneutralization of TGF-β1 in this model suggests that the course of scar production can be changed, particularly reduced or prevented. The development of novel therapies based on the manipulation of growth factor bioavailability within the wound in the acute phase of the injury response is a novel strategy.

The results of the studies relating to the present invention clearly implicate TGF-β1 as a regulator of scar production after a penetrating injury to the brain or spinal cord. Furthermore, because this scar formation can preclude neuronal recovery, the results indicate a potential use for TGF-β1 antagonists as an adjunct to those therapies designed to promote regeneration and reconnection of damaged neural pathways.

Accordingly, the present invention provides a method for preventing, suppressing or treating CNS pathologies characterized by a deleterious accumulation of extracellular matrix in a tissue. Such methods can be accomplished by contacting the tissue with an agent that inhibits the extracellular matrix producing activity of TGF-β1. The agent can be, for example, a neutralizing anti-TGF-β antibody or a functional fragment, or an Arg-Gly-Asp-containing peptide. Preferably, such an Arg-Gly-Asp-containing peptide is between 4 and 50 amino acids in length.

Additionally, agents that act as TGF-β antagonists, such as fragments of TGF-β having sequences that bind to a TGF-β receptor, can be used in the present methods. Such antagonists' should not induce the production of extracellular matrix, but will competitively bind to such receptors to prevent TGF-β binding.

The agent can also be decorin or its functional equivalent. As used herein, "decorin" refers to a proteoglycan having substantially the structural characteristics attributed to it in Krusius and Ruoslahti, *PNAS (USA)* 83:7638 (1986). Human fibroblast decorin has substantially the amino acid sequence presented in Krusius and Ruoslahti, supra. "Decorin" refers both to the native composition and to modifications thereof which substantially retain the functional characteristics. Decorin core protein refers to decorin that no longer is substantially substituted with glycosaminoglycan and is included in the definition of decorin. Decorin can be rendered glycosaminoglycan-free by enzymatic treatment, mutation or other means, such as by producing recombinant decorin in cells incapable of attaching glycosaminoglycan chains to a core protein or by synthesizing the core protein, all by means well known in the art.

Functional equivalents of decorin include modifications of decorin that retain its functional characteristics and molecules that are homologous to decorin, such as biglycan and fibromodulin, for example, that have the similar functional activity of decorin. Modifications can include, for example, the addition of one or more side chains that do not interfere with the functional activity of the decorin core protein.

The agents useful in the methods can be obtained by purifying the native protein or by proteolytic digestion of such proteins to obtain functionally active fragments according to methods known in the art. Alternatively, such agents can be synthesized or produced recombinantly by methods known in the art.

The present invention further provides methods for preventing, suppressing or treating a CNS pathology characterized by the insufficient accumulation of extracellular matrix components to promote scar formation. These methods can be accomplished by administering TGF-β or a functional fragment that promotes extracellular matrix production to a patient in need of such therapy. Such methods can be used when inadequate scar formation can or does result in a CNS pathology.

Pharmaceutical compositions containing agents that inhibit the activity of TGF-β or increase the concentration of TGF-β and a pharmaceutically acceptable carrier can be administered to a patient to prevent, enhance or otherwise treat CNS scar formation. Suitable pharmaceutically acceptable carriers include, for example, hyaluronic acid and aqueous solutions such as bicarbonate buffers, phosphate buffers, Ringer's solution and physiological saline supplemented with 5% dextrose or human serum albumin, if desired. Other pharmaceutical carriers known to those skilled in the art are also contemplated. The pharmaceutical compositions can also include other reagents that are useful for the prevention or treatment of the various CNS pathologies characterized or associated with the accumulation of extracellular matrix. The dosage of such pharmaceutical compositions can be readily determined by those skilled in the art based on various factors such as, for example, the type and extent of the injury, the age of the patient and the agent used.

The present invention further relates to methods of detecting the presence of various CNS pathologies of a tissue characterized by an excessive accumulation of extracellular matrix components by determining the level of TGF-β1 in the tissue. Such detection methods can be accomplished by the procedures described in the examples below or by other methods known in the art.

The following examples are intended to illustrate but not limit the invention.

EXAMPLE I

Materials

Unless specified, all reagents were analytical grade from Sigma Chemical Co. Ltd. (St. Louis, Mo.) or Poole (United Kingdom). Radioisotopes were obtained from Amersham International (Arlington Heights, Ill.). Recombinant human TGF-β1 was obtained from R and D Systems (Minneapolis, Minn.). Two anti-TGF-β1 antibodies were used in this study. The inactivating antibody used in the infusion experiments was raised in the turkey against intact native human TGF-β1. A different antibody was used for histochemistry, which was raised in the rabbit against amino acids 1–30 of human TGF-β1. Both of the anti-TGF-β1 antibodies were prepared and characterized by M. B. Sporn and K. C. Flanders (National Institutes of Health, Bethesda, Md.) and described in Logan et al., supra.

EXAMPLE II

Animals and Surgery

Surgical and animal care procedures were carried out with strict adherence to the guidelines set out in the "NIH guide for the care and use of laboratory animals," National Institutes of Health Publications No. 80–23. Groups of adult, female Sprague-Dawley rats (250 grams) were used in the study. Animals were anaesthetized with an intraperitoneal injection of a mixture of acepromazine (1.875 mg/kg), ketamine (3.75 mg/kg) and xylazine (1.9 mg/kg). Following craniotomy, a stereotactically defined, 4 mm deep, rostro-caudal knife-wound incision was made vertically into the right occipital cortex, corpus callosum and presubiculum, placed 1 mm anterior to Bregma/1.4 mm lateral of the mid-line, so it penetrated the anterior lateral ventricle at some point in its length. Control animals underwent craniotomy but no lesion was made.

Three days after surgery, four lesioned and two control rats were put under deep anaesthesia with the same anaesthetic and perfused transcardially with 300 ml of 0.9% (wt/vol) saline, 250 ml of 4% (wt/vol) paraformaldehyde (PFA) in 0.1 M acetate buffer, pH 6.5, followed by 500 ml of 4% (wt/vol) PFA plus 0.05% (wt/vol) glutaraldehyde in 0.1 M borate buffer, pH 9.5, using the pH shift method described in Simmons et al., *J. Histotechnology* 12:169–181 (1989), incorporated herein by reference. The brains were removed and post-fixed overnight at 4° C. in 4% (wt/vol) PFA in 0.1 M borate buffer containing 10% (wt/vol) sucrose. These brains were processed for in situ hybridization and immunoperoxidase staining to reveal expression of TGF-β1 mRNA and protein in the tissue surrounding the lesion.

The remaining three groups of six animals underwent a further surgical procedure at the same time as the placement of the lesion. In these animals, a vertical stainless steel cannula was inserted through the cranium into the posterior of the right lateral ventricle. The cannula was cemented into place with a dental cement platform which was stabilized by three stainless steel machine screws inserted into the cranium distal to the site of cannulation. The cannula was attached under the skin, via a flexible vinyl catheter, to a ready-primed Alzet mini-osmotic pump (model 2002, Alza Corporation, Palo Alto, Calif.) which was inserted into a sub-cutaneous pouch made in the dorsal neck region of the animal. The pumps supplied test agents to the cannula at a prescribed rate (0.5 μl/hr) and dose over a 14 day period.

In the main experiment the mini-osmotic pumps were primed to supply a basic infusion vehicle of phosphate-buffered artificial cerebrospinal fluid: 150 mM NaCl, 1.8 mM $CaCl_2$, 1.2 mM $MgSO_4$, 2.0 mM $K_2HPO_4$, 10.0 mM glucose, pH 7.4. In addition, 0.1% autologous rat serum was included in the vehicle to reduce absorption losses within the infusion apparatus. TGF-β1 protein and anti-TGF-β1 antiserum were diluted to their appropriate concentrations directly into this vehicle. In vitro experiments to monitor the stability of the infused TGF-β1 and anti-TGF-β1 antibody indicated that biological activity of both protein and antibody is preserved at 37° C. over a 14 day period. Six animals were infused with vehicle containing a 1:100 dilution of non-immune turkey serum (controls), six animals with vehicle containing a 1:100 dilution of turkey anti-TGF-β1 antiserum raised in turkeys against native human TGF-β1, and six animals with vehicle containing 150 ng/ml recombinant human TGF-β1. Thus, the TGF-β1-infused animals received 1.8 ng/day recombinant human TGF-β1 and the antiserum-infused animals received 0.12 μl/day non-immune or anti-TGF-β1 turkey antiserum. Fourteen days after cannula implantation and continuous delivery of experimental infusion solutions, all animals were processed as previously described and histochemical evaluation of the lesion site was performed by immunofluorescent staining.

EXAMPLE III

In Situ Hybridization of TGF-β1 mRNA

In situ hybridization of TGF-β1 mRNA used the Hind III-Xba I fragment of 0.985 kBp, derived from the major coding region of the rat TGF-β1 precursor (Qian et al., *Nucl. Acids Res.* 18:3059 (1990)), which was sub-cloned into pBluescript SK+ (Stratagene, San Diego, Calif.). The antisense RNA strand of the coding sequence was transcribed using T7 polymerase and $^{35}$S-UTP according to manufacturer's instructions. $^{35}$S-UTP labelled RNA probes encoding sense strands of 5' non-coding sequences were prepared with T3 RNA polymerase and used for alternate control tissue sections.

The fixed brains were frozen in O.C.T. compound (Miles Laboratories Inc., Napeville, Ill.) in dry ice and stored at −80° C. At a later date, 20 μm frozen sections were cut and collected in cryoprotectant solution (50% 0.05 M sodium phosphate buffer, pH 7.3, 30% ethylene glycol and 20% glycerol) and stored at −20° C. Subsequently cryoprotected brain sections were washed thoroughly in phosphate-buffered saline (PBS), mounted on poly-L-lysine coated slides, dried under vacuum and stored at -80° C. until use.

For analysis, sections were digested with 10 μg/ml of proteinase K in 0.1 M Tris (pH 8.0) containing 50 mM EDTA at 37° C. for 30 minutes and then rinsed in deionized water, followed by an incubation in 0.1 M triethanolamine hydrochloride (TEA), pH 8.0 for 3 minutes. Sections were acetylated for 10 minutes with 0.25% (wt/vol) acetic anhydride in 0.1 M TEA, rinsed in 2×SSC (prepared from a 20×stock solution which contains 3 M NaCl and 0.015 M sodium citrate), dehydrated through a graded series of ethanol washes and then air dried for 2 hours before hybridization.

Hybridization with the labelled TGF-β1 antisense or sense probes (1×10$^7$ cpm/ml) was performed at 55° C. overnight in 10 mM Tris (pH 8.0) containing 50% (wt/vol) formamide, 0.3 M NaCl, 1 mM EDTA, 10 mM dithiothreitol (DTT), 1×Denhardt's solution (0.1 g Ficoll 400, 0.1 g polyvinylpyrrolidone, 0.1 g of bovine serum albumin), and 10% (wt/vol) dextran sulfate. After hybridization, sections were rinsed for 1 hour in 4×SSC and treated with 25 μg/ml of ribonuclease A in 10 mM Tris (pH 8.0) containing 0.5 M NaCl, 1 mM EDTA at 37° C. for 30 minutes. This treatment was followed by increasing high stringency washes of SSC containing 1 mM DTT, followed by a final wash in 0.1×SSC at 65° C. for 30 minutes.

Slides were then dehydrated through a graded series of ethanol, until absolute ethanol, dried under vacuum and exposed to βmax hyperfilm (Amersham) for 5 days at 4° C. to examine gross changes in mRNA. For microscopic analysis, slides were coated with Kodak NTB-2 liquid autoradiograph emulsion and exposed at 4° C. for 2–3 weeks. They were developed in Kodak D-19, rinsed briefly in water, and fixed in Kodak rapid fixer. After washing in distilled water for at least 45 minutes, slides were counterstained with Harris' haematoxylin in order to visualize the cells. Silver grains were examined by dark field and bright field microscopy.

Bright and dark field views of the lesion site were taken. After three days, an intense signal was observed for TGF-β1 mRNA in the neuropile bordering the lesion site. This focal elevation of TGF-β1 mRNA suggests a local expression of TGF-β1 within the damaged neural tissue in response to injury. Under higher power, the bright field view revealed that the signal was mainly associated with cells of neuronal and astrocytic visual phenotype, although signal was also seen associated with endothelial cells of the microvasculature and in the local meninges. The increased level of signal seen in the lesioned hemisphere was striking when compared to that seen in the contralateral hemisphere or in sections of unlesioned brain, which were processed identically and simultaneously. Since the signal observed in the brains of control animals was also minimal, it seems that there is normally very low expression of TGF-β1 mRNA in this tissue. The hybridization signal observed in sections from lesioned rat brains was specific, since adjacent tissue sections hybridized with the sense strand of cRNA show no signal.

EXAMPLE IV

Immunoperoxidase Staining of TGF-β1

Immunoperoxidase staining for TGF-β1 in 20 μm frozen sections of brain was accomplished using the ABC Vactastain Elite kit (Vector Laboratories Ltd., Burlingame, Calif.) according to the manufacturer's instructions. The primary antiserum raised against TGF-β1 has been previously described and characterized in Flanders et al., *J. Cell Biol.* 108:653–660 (1989). It is an IgG fraction of a rabbit polyclonal, raised against amino acids 1–30 of human TGF-β1, which was purified by passage over a protein A-Sepharose column.

For analysis, the cryoprotected 20 μm sections were washed thoroughly in PBS, mounted onto gelatin coated slides, rinsed again in PBS and the endogenous peroxidase was quenched by incubating the sections in 0.3% (vol/vol) hydrogen peroxide in PBS for 30 minutes. The sections were rinsed in PBS and incubated for 30 minutes in 1.5% (vol/vol) normal goat serum, diluted in PBS containing 0.3% (vol/vol) Triton X-100, in order to block non-specific binding. Following this procedure, the sections were incubated for 24 hours at 4° C. with protein-A purified rabbit anti-TGF-β1 antibody (0.015 mg/ml) diluted in PBS containing 0.3% (vol/vol) Triton X-100 and 1% (wt/vol) bovine serum albumin (BSA). They were then rinsed and incubated with a 1:200 dilution of biotinylated goat anti-rabbit IgG (Vector) for 45 minutes, rinsed and incubated with avidin-biotin-peroxidase complex (Vector) for 30 minutes. After rinsing in PBS, the sections were treated with 0.5 mg/ml of 3'3'-diaminobenzidine (DAB), diluted in PBS containing 0.01% (vol/vol) hydrogen peroxide for 5 minutes. All steps were separated by buffer washes consisting of PBS, pH 7.4, containing 0.3% (vol/vol) Triton X-100. The sections were finally washed in PBS, counterstained with Harris' haematoxylin, dehydrated, cleared, and mounted. Sections incubated with anti-TGF-β1 antibody pre-incubated with recombinant TGF-β1 or without primary antibody were used as controls. Sections processed with the control procedures failed to stain.

The immunocytochemical localization of TGF-β1 in the wound was determined three days after injury. The appearance of immunoreactive TGF-β1 seen in damaged neural tissue correlates with the extent of mRNA induction observed by in situ hybridization. Under high magnification, the predominant cell types (by morphological criteria) localizing strong TGF-β1 immunoreactivity three days after injury were the astrocyte and macrophage. The staining is mostly limited to damaged neural tissues bordering the forming glia limitans and thus appears to be primarily extracellular. In this study, no immunoreactivity was observed in the contralateral hemisphere or in sections of normal, unlesioned brain processed simultaneously.

EXAMPLE V

Immunofluorescent Staining of the Wound

After perfusion fixation, the brains of the fourteen day cannulated and continuously infused animals were washed in PBS overnight at 4° C., dehydrated in graded alcohols, embedded in polyester wax (melting point 37° C.) and stored at 4° C. Sections (7 μm) were cut on a microtome fitted with a cooled chuck and floated onto a gelatin solution (10 mg/ml) on subbed slides and air-dried.

The antibodies used to identify cellular changes in the wounds were rabbit anti-bovine glial fibrillar acidic protein (GFAP) as a marker of activated astrocytes, rabbit anti-mouse fibronectin to visualize matrix deposition within the wound and rabbit anti-mouse ED1 as a marker of cells of the macrophage/microglial lineage. All of these antibodies were obtained from Dakopatt Ltd. (High Wycombe, U.K.) and were used at a dilution of 1:200 in PBS containing 1% (wt/vol) BSA.

The mounted brain sections were dewaxed, rehydrated and placed in PBS containing 0.1% (vol/vol) Tween-20 for 15 minutes. They were then incubated in the specific antibody for 1–12 hours at room temperature. After three washes in PBS, sections were incubated in goat anti-rabbit IgG conjugated with fluorescein isothiocyanate (FITC, Sigma), diluted to 1:100. The sections were washed in three changes of PBS and mounted in a non-quenching mountant. For controls, either the first or second antibody was omitted, all were negative. The sections were examined with an Olympus BH-2 microscope with a fluorescent attachment. Photomicrographs were taken on Ilford HP5 film, rated at 400 ISO.

EXAMPLE VI

General Appearance of the Lesion

Three days after the induced injury, oedema in the wound was still extensive. Many macrophages were present in the central lumen of the wound but macrophages and microglia were also seen in the damaged neuropile. Numerous meningeal-fibroblasts were present in the center of the wound in the superficial cortex and scar tissue was beginning to form between the cut edges of the cortical neuropile, but had not yet penetrated the depths of the lesion. Reactive astrocytes were particularly numerous at the damaged margin of the neuropile, and also extended well into the intact neuropile.

At 14 days the major cellular events are complete. Briefly, the scar tissue had contracted, bringing the cut borders of the neuropile close together. Some residual macrophages were visible in the fibrous tissue which had been deposited at the center of the lesion site. A fully developed glia limitans was present that lines the cut margins of the neuropile and surrounds a thin core of fibrous scar tissue. Reactive astrocytes were still visible through the damaged and intact neuropile, but the gliosis was receding.

EXAMPLE VIII

Characterization of the Wound After Infusion of Recombinant TGF-β1 and TGF-β1 Neutralizing Antibodies The efficacy of the infusion method for the delivery of test agents to cells at the site of cannulation and at the site of lesion was tested by infusing a 1:100 dilution of non-immune rabbit antiserum into the right lateral ventricle of two lesioned rats over a two week period (0.12 μl antiserum/day directly into the CSF). After fixation by perfusion, the brains were processed for immunoperoxidase staining using an anti-rabbit IgG antibody (Dakopatt Ltd., High Wycombe, U.K.), to examine the extent of penetration of the infused antiserum. The results of this test show an extensive distribution of the infusate is revealed throughout the tissue surrounding both the site of cannulation and the site of lesion.

Penetration of infused recombinant protein and antiserum into the tissue surrounding the lesion site was confirmed at fourteen days in each experimental animal by immunoperoxidase staining. By this time the endogenous expression of TGF-β1 has virtually subsided and negligible TGF-β1 is detectable in the control, vehicle-infused animals. There was no observed effect of any of the continuous infusions into the CSF on the gross morphology of the ventricles, assessed by visual and microscopic inspection of tissue sections. The effect on the injury response of modulating TGF-β1 availability at the wound site by continuous infusion of TGF-β1-related molecules is discussed in more detail below. Briefly, the TGF-β1 infused wounds show a normal reactive gliosis response, an abnormal amount of fibronectin deposition and an increased number of macrophage and microglial cells when compared to control. The anti-TGF-β1 antiserum infused animals show a normal reactive gliosis response, but no organization of astrocytes to form a limiting glia limitans at the margins of the damaged neuropile. There is also a complete absence of immunoreactive fibronectin within the wound and a reduced number of macrophage/microglial cells when compared to control.

A. Control, Vehicle Infusions

In rats with wounds that had been continuously infused with vehicle plus non-immune turkey IgG, immunofluorescent staining of sections after 14 days shows the scar tissue has contracted bringing together the cut borders of the neuropile. In the center of the wound was a thin layer of fibrous tissue represented by the fluorescent fibronectin, which is visible after staining with anti-fibronectin antibody.

Anti-ED1 antibody, which detects cells of the macrophage/ microglial lineage, revealed residual cells in the center of the wound and in neural tissues bordering the scar. GFAP-positive astrocytes were still abundant in the tissue around the wound and are particularly numerous at the lesion edge, where they associate to construct a glia limitans which helps to reform the blood-brain barrier. The scar of these animals was deemed to be normal when compared to scars seen in lesioned, non-infused rats.

B. Recombinant TGF-β1 Infusions

Continuous infusion of the wound with 1.8 ng/day recombinant human TGF-β1 resulted in a clear enhancement of scarring with matrix deposition being markedly increased compared to lesioned, non-infused rats. The increase in matrix deposition was evidenced by the presence of an abnormally large area of immunoreactive fibronectin in the center of the wound, which resulted in a wide separation of the normally closely apposed cut faces of the neuropile. The fibronectin deposition was accompanied by an exactly coincident increase in collagen IV and laminin deposition. TGF-β1 treatment also dramatically increased the number of residual macrophage/microglia cells in the neuropile, which was detected by using anti-ED 1 antibody, but had no apparent effect on the extent of reactive gliosis observed, which was visualized with anti-GFAP antibody. The continuous glia limitans, formed by the reactive astrocytes and marking the borders of the cut neuropile, was evident in these wounds.

C. Anti-TGF-β1 Antiserum Infusions

Immunoneutralization of endogenous TGF-β1 with 0.12 μl/day of turkey anti-TGF-β1 antiserum confirmed the effects of exogenous TGF-β1 observed above. In direct contrast, this treatment markedly reduced the amount of fibrous scar tissue deposited in the wound. In this experiment, the extent of scar reduction was variable, four out of six rats responding to the treatment, with two of these showing an almost complete absence of matrix deposition in the wound. One such animal showed no apparent fibronectin deposition in the wound after fourteen days, as indicated by the absence of fibronectin immunoreactivity and a reduced residual number of ED 1-expressing macrophages/ microglia. The neural tissue around this wound contained numerous reactive GFAP-positive astrocytes. However, these have not become organized into a limiting glial membrane at the margin of the lesion.

Although the invention has been described with reference to various embodiments, it should be understood that various modifications can be made without departing from the spirit or scope of the invention. Accordingly, the invention is limited only by the following claims.

We claim:

1. A method useful for suppressing a deleterious accumulation of extracellular matrix in a tissue of the central nervous system, comprising administering to the tissue an agent that binds to TGF-β and that inhibits the extracellular matrix producing activity of TGF-β in an amount effective to inhibit extracellular matrix accumulation.

2. The method of claim 1, wherein the deleterious accumulation of extracellular matrix in a tissue of the central nervous system results in scar formation.

3. The method of claim 1, wherein said agent is a neutralizing anti-TGF-β antibody.

4. The method of claim 1, wherein said agent is decorin.

5. The method of claim 1, wherein said agent is biglycan.

6. The method of claim 1, wherein said TGF-β is TGF-β1.

7. The method of claim 1 wherein the said agent is fibromodulin.

8. A method useful for suppressing scar formation in a lesion of central nervous tissue comprising administering to the tissue an agent that inhibits the extracellular matrix producing activity of TGF-α, wherein said agent is decorin, biglycan, fibromodulin or a neutralizing anti-TGF-β antibody, in an amount effective to inhibit extracellular matrix accumulation.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 112 amino acids
      (B) TYPE: amino acid
      (D) TOPOLOGY: linear (xi) SEQUENCE DESCRIPTION: SEQ ID NO:1:

```
Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
                100                 105                 110
```